(12) United States Patent
Leipzig et al.

(10) Patent No.: US 11,760,991 B2
(45) Date of Patent: Sep. 19, 2023

(54) MULTI-FUNCTIONAL OXYGENATING MICROPARTICLE LOADED CELL AGGREGATES

(71) Applicants: Nic Leipzig, Hudson, OH (US); Pritam Patil, Worchester, MA (US)

(72) Inventors: Nic Leipzig, Hudson, OH (US); Pritam Patil, Worchester, MA (US)

(73) Assignee: The University of Akron, Akron, OH (US)

( * ) Notice: Subject to any disclaimer, the term of this patent is extended or adjusted under 35 U.S.C. 154(b) by 313 days.

(21) Appl. No.: 17/046,921

(22) PCT Filed: Apr. 12, 2019

(86) PCT No.: PCT/US2019/027135
§ 371 (c)(1),
(2) Date: Oct. 12, 2020

(87) PCT Pub. No.: WO2019/200197
PCT Pub. Date: Oct. 17, 2019

(65) Prior Publication Data
US 2021/0147825 A1 May 20, 2021

Related U.S. Application Data

(60) Provisional application No. 62/656,519, filed on Apr. 12, 2018.

(51) Int. Cl.
*C12N 11/10* (2006.01)

(52) U.S. Cl.
CPC .......... *C12N 11/10* (2013.01); *C12N 2531/00* (2013.01); *C12N 2533/00* (2013.01); *C12N 2533/70* (2013.01)

(58) Field of Classification Search
CPC ......... C08B 37/003; C08L 5/08; C12N 11/10; C12N 2500/02; C12N 2531/00; C12N 2533/00; C12N 2533/30; C12N 2533/70; C12N 5/0012
See application file for complete search history.

(56) References Cited

U.S. PATENT DOCUMENTS

| 4,742,050 A | 5/1988 | Yuhas et al. |
| 4,781,676 A | 11/1988 | Schweighardt et al. |
| 5,155,034 A * | 10/1992 | Wolf .................... C12N 5/0062 435/402 |
| 6,759,242 B1 * | 7/2004 | Csete .................... C12N 5/0623 435/375 |
| 2003/0199687 A1 | 10/2003 | Yalpani |

FOREIGN PATENT DOCUMENTS

| WO | 2008157318 | 12/2008 |
| WO | 2013112863 | 8/2013 |

* cited by examiner

*Primary Examiner* — Blaine Lankford
(74) *Attorney, Agent, or Firm* — RENNER KENNER GREIVE BOBAK TAYLOR & WEBER

(57) ABSTRACT

A method of preparing and obtaining cell aggregates having increased oxygenation abilities. The method includes the preparation of fluorinated polymeric microparticles. Once the fluorinated polymeric microparticles are prepared, they are combined with mammalian cells to create the cell aggregates having increased oxygenation.

13 Claims, 4 Drawing Sheets
(4 of 4 Drawing Sheet(s) Filed in Color)

MULTI-FUNCTIONAL OXYGENATING MICROPARTICLE LOADED CELL AGGREGATES

CROSS-REFERENCE TO RELATED APPLICATIONS

This application claims priority to U.S. Provisional Patent Application No. 62/656,519 entitled "Multifunctional Oxygenating Microparticles for Organogenesis and Organ Therapy", filed on Apr. 12, 2018, the contents of which are incorporated herein by reference.

STATEMENT REGARDING FEDERALLY SPONSORED RESEARCH OR DEVELOPMENT

This invention was made with government support under R15GM104851 awarded by the National Institute of Health. The government has certain rights in the invention.

FIELD OF THE INVENTION

The present invention generally relates to multicellular cell aggregates loaded with oxygenating microparticles. More particularly, the present invention relates to cellular aggregates loaded with fluorinated polymer microparticles. In one or more embodiments, the present invention relates to cell aggregates loaded/mixed with chitosan microparticles with immobilized perfluorocarbons so as to reduce cell hypoxia in the core of the cell aggregates.

BACKGROUND OF THE INVENTION

Only one in a thousand new drug formulations that enter preclinical studies ever enter into human clinical trials, and only one out of five of those that make it into human clinical trials is ever approved. Thus, the chance of new drug formulation being approved is one in five-thousand. Billions of dollars are invested in finding and testing potential drug candidates, and typically preclinical animal models are employed that do not necessarily provide a result that translates into humans. Therefore, the prescreening of drug molecules in humanized platforms can potentially decrease failure rates during the drug discovery process. Currently, emerging drug screening technologies such microfluidic organs on-a-chip, micro-patterned cultures, bio-printed organoids, and randomly organized organoids present promising solutions to drug screening.

Cell aggregates are cells that are grouped together that bound, secrete and assemble extracellular matrixes in order to form simple unicellular random organization or higher order multicellular organization forming Spheroids and Organoids respectively. Organoids are related to a higher order of cell assemblies due to their organ-like structures. Their structures are characterized by having distinguishable layers such as epithelia and mesenchyme. Human cell-based organoids therefore present a more realistic and comparable model for drug screening. Organoids not only present potential as drug screening platforms but also can be used for disease modeling studies, and organ transplantation research. Organoids are a miniaturized and simplified version of organs comprising three-dimensional microanatomy of several differentiated and progenitor cells. Spheroids, as compared to organoids are more irregular and are seen as aggregates of cells. Spheroids present a simple alternative model and reduce the complexity of using organoids.

Spheroids have been studied for oxygen gradients in a 3D environment. Previously, oxygen zonation has been clearly defined and studied in spheroids and zones such as high proliferation zones, low proliferation zones, hypoxic zones and necrotic cores have been identified. However, a common challenge that remains true for organoids and spheroids alike is oxygen perfusion to create larger functional tissues in vitro. Oxygen is vital for tissue development and growth and is a preferred mammalian energy source, and many approaches to regenerative in vitro, ex vivo, and in vivo tissue engineering fail due to an insufficient oxygen supply. Oxygen promotes cell proliferation and protein synthesis while limiting the harmful effects of hypoxic environments. Past attempts to improve oxygen transport in organoids and spheroids have included the use of artificial microvessels, direct fluid perfusion, and oxygen vesicles for oxygen transport. Despite these efforts, insufficient oxygenation of organoids and 3D tissues limits the size of organoids that can be produced and consequently limits their application and suitability to drug screening.

There is a need in the art for means for providing enough oxygen to organoids and spheroids such that a hypoxic environment is not formed.

SUMMARY OF THE INVENTION

In a first embodiment, the present invention provides a method for obtaining cell aggregates having increased oxygenation, the method comprising the steps of preparing fluorinated polymeric microparticles and combining the fluorinated polymeric microparticles with mammalian cells to create the cell aggregates having increased oxygenation.

In a second embodiment, the present invention provides a method for obtaining cell aggregates as in any embodiment above, wherein the step of preparing the fluorinated polymeric microparticles utilizes a method selected from the group consisting of a mini-emulsion method, electro-spraying, microfluidics, and flow focusing.

In a third embodiment, the present invention provides a method for obtaining cell aggregates as in any embodiment above, wherein the method is a mini-emulsion method and wherein the mini-emulsion method includes the steps of pumping a solution of a fluorinated polymer and an acidic buffer into a stirred solution of a fatty alcohol and a surfactant using a syringe pump and then crosslinking with a crosslinking reagent.

In a fourth embodiment, the present invention provides a method for obtaining cell aggregates as in any embodiment above, wherein the fluorinated polymer includes polymers having polysaccharide backbone chains and wherein the polysaccharide backbone chains have a pendant fluorine containing group attached thereto.

In a fifth embodiment, the present invention provides a method for obtaining cell aggregates as in any embodiment above, wherein the polysaccharide backbone chains include a polysaccharide unit defined by the formula:

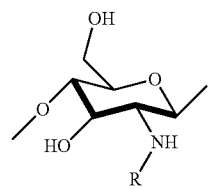

where R is a fluorine containing group.

In a sixth embodiment, the present invention provides a method for obtaining cell aggregates as in any embodiment above, wherein the polysaccharide backbone chains include one or more saccharide units that include an alkene group selected from the group consisting of:

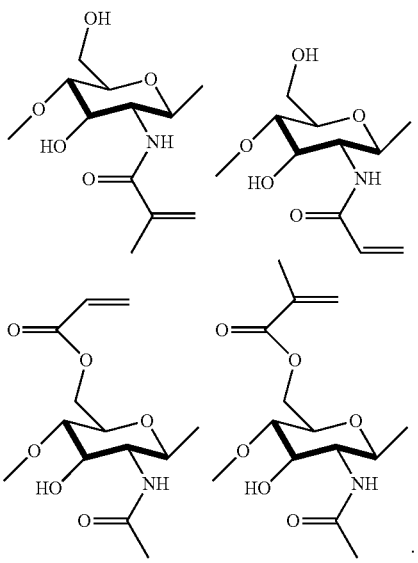

In a seventh embodiment, the present invention provides a method for obtaining cell aggregates as in any embodiment above, wherein the fluorinated polymer is defined by the formula:

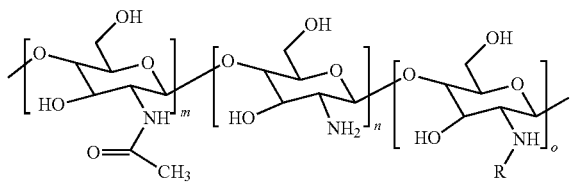

where R is a fluorine containing group, m is about 0% to about 20% of the total saccharide units, n is about 50% to about 95% of the total saccharide units, and o is about 1% to about 40% of the total saccharide units.

In an eighth embodiment, the present invention provides a method for obtaining cell aggregates as in any embodiment above, wherein the solution of the fluorinated polymer and the acidic buffer is pumped into the stirred solution of the fatty alcohol and surfactant at a rate of between about 1 µL/min to about 30 µL/min.

In a ninth embodiment, the present invention provides a method for obtaining cell aggregates as in any embodiment above, wherein the solution of the fluorinated polymer and the acidic buffer is pumped into the solution of the fatty alcohol and surfactant that is being stirred at a rate of between about 400 rpm and about 1200 rpm.

In a tenth embodiment, the present invention provides a method for obtaining cell aggregates as in any embodiment above, wherein the mammalian cells are selected from the group consisting of dermal fibroblasts, stem cells, neural stem cells, liver cells (e.g., hepatocytes, stellate cells, sinusoid cells), neural stem cells, intestinal epithelia cells, stomach cells, colon cells, kidney cells, pancreas cells, lymphatic cells, vascular cells, bone cells, bone marrow cells, cardiac cells, brain cells, nerve cells, spinal cord cells, skin cells, fat cells, cancer cells, glandular cells, or reproductive cells.

In a eleventh embodiment, the present invention provides a method for obtaining cell aggregates as in any embodiment above, wherein the cell aggregates having increased oxygenation have a partial oxygen pressure 24 hours after being combined with the fluorinated polymeric microparticles that is greater that the partial oxygen pressure of the mammalian cells at the time of combination with the fluorinated polymeric microparticles.

In a twelfth embodiment, the present invention provides a method for obtaining cell aggregates as in any embodiment above, wherein the fluorinated polymeric microparticles are combined with the mammalian cells in a centrifuge at a speed of from about 200 rpm to about 2,000 rpm.

In a thirteenth embodiment, the present invention provides a method for obtaining cell aggregates as in any embodiment above, wherein the obtained cell aggregate contains between about 10% and about 75% volume percent fluorinated polymer microparticles.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the features and advantages of the present invention, reference is now made to the detailed description of the invention along with the accompanying figures in which.

DETAILED DESCRIPTION OF ILLUSTRATIVE EMBODIMENTS

In some embodiments, the present invention provides cellular aggregates loaded with oxygenating microparticles. In some embodiments, the present invention provides cellular aggregates loaded with fluorinated polysaccharide microparticles. In some embodiments, the present invention provides cellular aggregates loaded with chitosan microparticles with immobilized perfluorocarbons so as to reduce cell hypoxia, especially in the core of the aggregates.

For decades researchers have demonstrated the importance of oxygen in sustaining cell proliferation, differentiation, and signaling processes. Oxygen has been a critical limiting factor in the growth of larger and complex organoids. The vast majority of cell aggregates are the preparation of organoids and spheroids that are then used for disease modeling while continually struggling with lack of proper perfusion. Some postulate that oxygen consumption levels and local oxygen zonation might affect the function of these cell aggregates significantly. Therefore, the ability to improve localized oxygen transport properties within organoids offers the unprecedented advantage of growing increasingly complex and large organoids, which were previously impossible due to hypoxic core formation and reduced cell viability.

Figure 1:
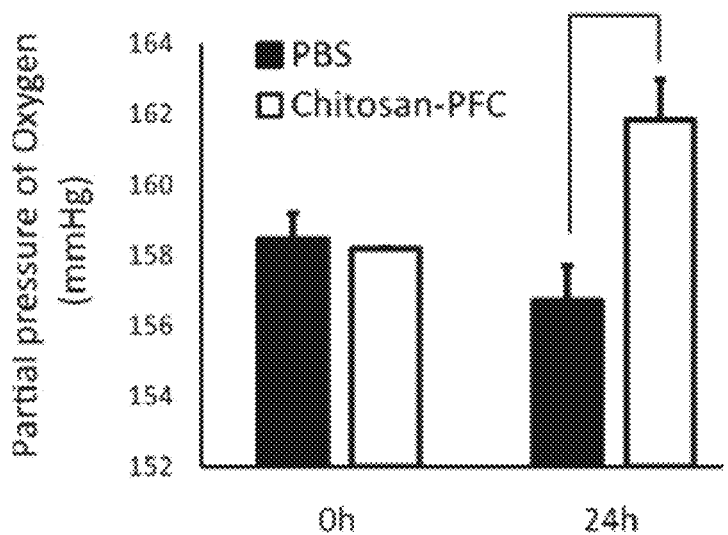
FIG. 1 is a graphical representation of the partial pressure of oxygen of fluorinated polymeric microparticles in a phosphate buffer solution (PBS) as compared to a control of PBS with no particles.

The selection of fluorinated chitosan offers a platform for enhancing oxygen transport properties in the 3D cellular environment by sequestering oxygen from its surrounding atmosphere and maintaining high local oxygen concentration even in the center of a cell aggregate. Namely, the present invention shows that oxygenating microparticles can be successfully prepared from fluorinated chitosan while utilizing a modified microfluidics mini-emulsion method resulting in a narrow distribution of small sizes of microparticles. As shown in FIG. 1, oxygen transport into fluorinated chitosan microparticles from the surrounding environment in a cell culture incubator is shown to be higher than a phosphate buffer saline (PBS) control over a twenty-four hour period. Cell aggregates prepared with an increased loading percentage of microparticles as compared to cell aggregates prepared without the microparticles were shown to have a direct correlation between the number of particles and the reduction in hypoxia and necrosis.

In one or more embodiments, the microparticles are prepared from a crosslinked polymer containing a pendant fluorine containing group. The fluorine containing group causes the polymer to attract and dissolve oxygen, which can later be harnessed for areas of low oxygen concentration. For the purposes of this specification, the crosslinked polymer having pendant fluorine containing groups is referred to as a fluorinated polymer. The fluorinated polymer may absorb oxygen when moved from an initial environment to an environment of higher oxygen tension. The fluorinated polymer upon exposure to an environment of lower oxygen tension may then release oxygen.

In its broadest sense, a fluorine containing group is to be understood as a group that includes at least one fluorine atom. In one or more embodiments the fluorine is bonded directly to a carbon atom. In one or more embodiments, the fluorine containing group is a pendant fluorine containing group. A pendant fluorine containing group is pendantly attached to a polymer. In other words, a pendant fluorine containing group is a side chain that is attached to the main chain or backbone of a polymer.

In one or more embodiments, the fluorine containing group may be a fluorocarbon group. In one or more embodiments, a fluorocarbon group may be a hydrocarbon group where one or more hydrogen atoms are substituted with a fluorine atom. Suitable fluorocarbon groups that can be substituted with fluorine atoms include alkyl groups such as methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, and sec-hexyl. For the purpose of this disclosure, the term fluorocarbon and perfluorocarbon can be used interchangeably. For simplicity, perfluorocarbon may be abbreviated PFC.

In one or more embodiments a fluorocarbon group may be defined by the formula:

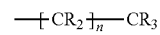

where each R is individually a hydrogen atom, or a fluorine atom with the proviso that at least one of the R groups is a fluorine atom. In one or more embodiments, n may range from 0 to 20. In one or more embodiments, n may range from 1 to 9. In one or more embodiments, n may range from 6 to 8.

Specific examples of fluorocarbon groups include —$CF_3$, —$(CF_2)_n$—$CF_3$ $(CF_2)_n$—$CF_3$, —$(CH_2)_n$—$CF_3$, and —$(CH_2)_n$—$(CF_2)_n$—$CF_3$. In one or more embodiments, n may range from 0 to 20. In one or more embodiments, n may range from 1 to 9. In one or more embodiments, n may range from 6 to 8.

In one or more embodiments, the fluorocarbon may be an aromatic fluorocarbon group. In one or more embodiments, an aromatic fluorocarbon group may be defined as an aromatic group where one or more hydrogen atoms are substituted with a fluorine atom. In one or more embodiments an aromatic fluorocarbon group may be defined by the formula:

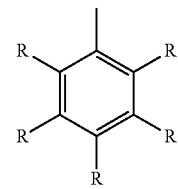

where each R is individually hydrogen atom, a fluorine atom, a hydroxyl group, a hydrocarbon group, or a fluorocarbon group, with the proviso that at least one of the R groups is a fluorine atom. Specific examples of aromatic fluorocarbon groups include

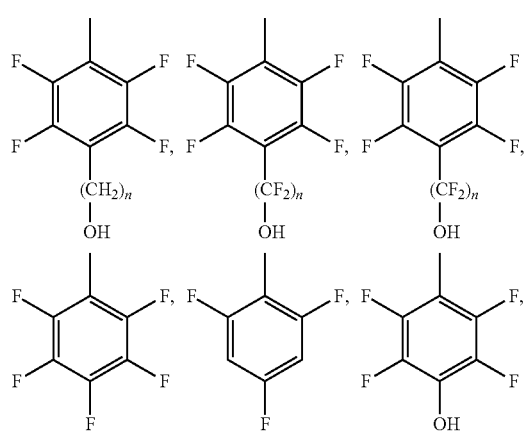

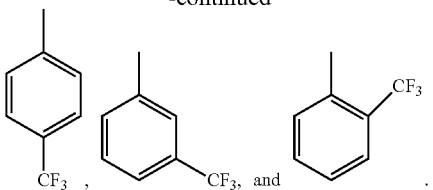

In one or more embodiments, n may range from 0 to 9. In one or more embodiments, n may range from 1 to 6. In one or more embodiments, n may range from 2 to 4.

In one or more embodiments, the fluorine containing group may be a carbonyl group defined by the formula:

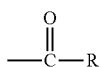

where R is a fluorocarbon group. Specific examples of carbonyl defined by the above formula include groups include

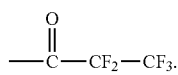

In one or more embodiments, the fluorine containing group may be a carboxylate group defined by the formula:

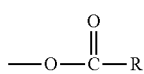

where R is a fluorocarbon group. Specific examples of carboxylate groups defined by the above formula include

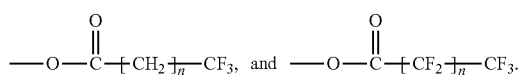

In one or more embodiments, n may range from 0 to 20. In one or more embodiments, n may range from 1 to 9. In one or more embodiments, n may range from 6 to 8.

In one or more embodiments, the polymer backbone of the fluorinated polymer used to make the microparticles have a more have an average molecular weight of between about 10,000 and about 300,000 Da. In one or more embodiments, the polymers have an average molecular weight of between about 100,000 and about 250,000 Da. In one or more embodiments, the polymers have an average molecular weight of between about 175,000 and about 225,000 Da.

In one or more embodiments, the polymer backbone of the fluorinated polymer used to make the microparticles include those with a reactable moiety. Suitable reactable moieties include hydroxyl groups, amino groups, carboxylic acid groups, sulfhydryl groups, maleimide groups, tyrosine/peptide groups, azide groups, dibenzyl cyclooctyne groups, trans-cyclooctene groups, norbornene groups, phosphine groups, biotin groups, avidin groups, tetrazine groups, alkyne groups, or combinations thereof.

Exemplary polymers include polyethylene glycol, poly (N-isoproylacrylamide), polyacrylamide, peptides/proteins or a combination thereof.

In one or more embodiments, the polymer backbone of the fluorinated polymer may be a polysaccharide. Exemplary polysaccharides include chitosan, dextran, hyaluronic acid, agarose, alginate, starch, cellulose, glycogen, carrageenans, galactomannans and combinations thereof.

In one or more embodiments, the polysaccharide is comprised of polymerized saccharide units. For the purpose of this specification a saccharide unit is a mer unit of a polysaccharide polymer. In one or more embodiments, the polysaccharide polymer can be comprised of saccharide units that have a functionality. In these or other embodiments, the polysaccharide polymer can comprise a saccharide unit that includes a fluorocarbon group and a saccharide unit that includes an alkene group. In one or more embodiments, the polysaccharide polymer may further comprise a saccharide unit that includes an acetylamino group. In these or other embodiments, the polysaccharide polymer may further comprise a saccharide unit that includes amino group.

In one or more embodiments, the polysaccharides, prior to crosslinking, may include a saccharide unit that includes a fluorocarbon group defined by the formula:

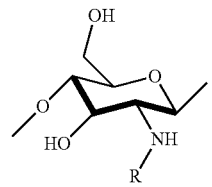

where R is a fluorine containing group.

In one or more embodiments, the polysaccharides, prior to crosslinking, may include a saccharide unit that includes a alkene group defined by one of the formula:

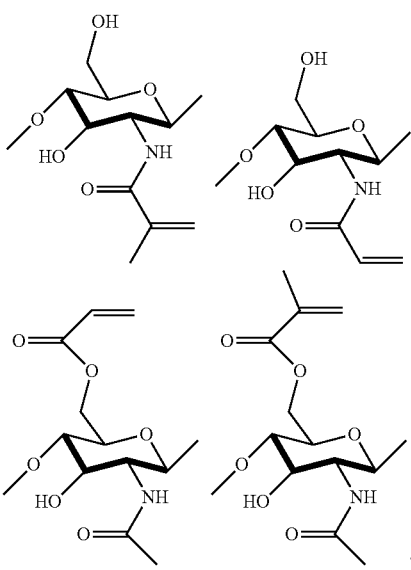

In one or more embodiments, the polysaccharides, prior to crosslinking, may include a saccharide unit that includes an acetylamino defined by the formula:

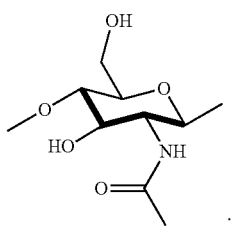

In one or more embodiments, the polysaccharides, prior to crosslinking, may include a saccharide unit that includes amino defined by the formula:

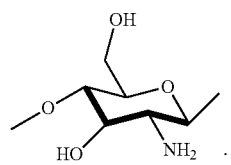

In one or more embodiments, the polysaccharide polymer, prior to crosslinking, is a random copolymer of saccharide units defined by the formula:

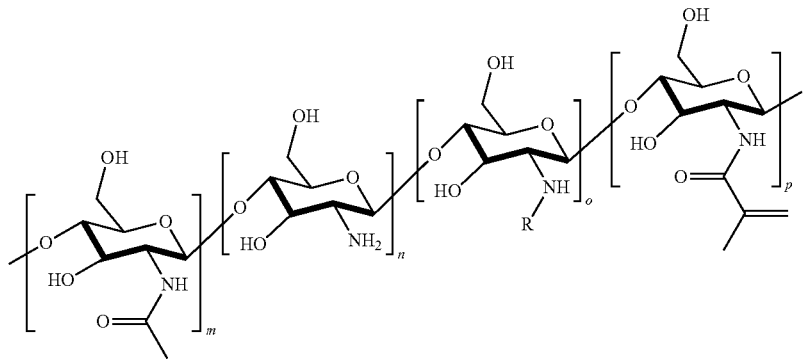

where R is a fluorine containing group as described above, m is about 0% to about 20% of the total saccharide units, n is about 15% to about 70% of the total saccharide units, o is about 1% to about 40% of the total saccharide units, and p is about 10% to about 30% of the total saccharide units.

In one or more embodiments, the polysaccharide polymer, prior to crosslinking, is a random copolymer of saccharide unites defined by the formula:

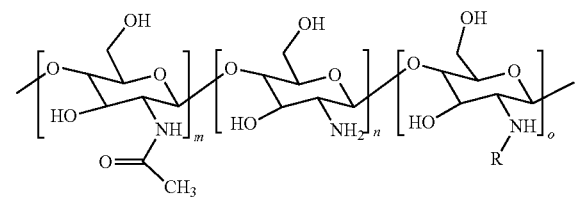

where R is a fluorine containing group as described above, m is about 0% to about 20% of the total saccharide units, n is about 50% to about 95% of the total saccharide units, and o is about 1% to about 40% of the total saccharide units.

Fluorinated polymers utilized in the present invention dissolve $O_2$ as well as other oxygenated species, such as $CO_2$, CO and NO, by diffusion. Thus, the fluorinated polymers utilized in the present invention may also be used to dissolve other molecules such as $CO_2$, CO, or NO alone or in combination with $O_2$.

The fluorinated polymers are prepared for use in creating fluorinated polymeric microparticles. In one or more embodiments, the method used to create the fluorinated polymeric microparticles is selected from the group consisting of mini-emulsion methods, electro-spraying methods, microfluidic methods, and flow focusing methods. In some embodiments, the method used to create the fluorinated polymeric microparticles is a mini-emulsion method.

Figure 2:
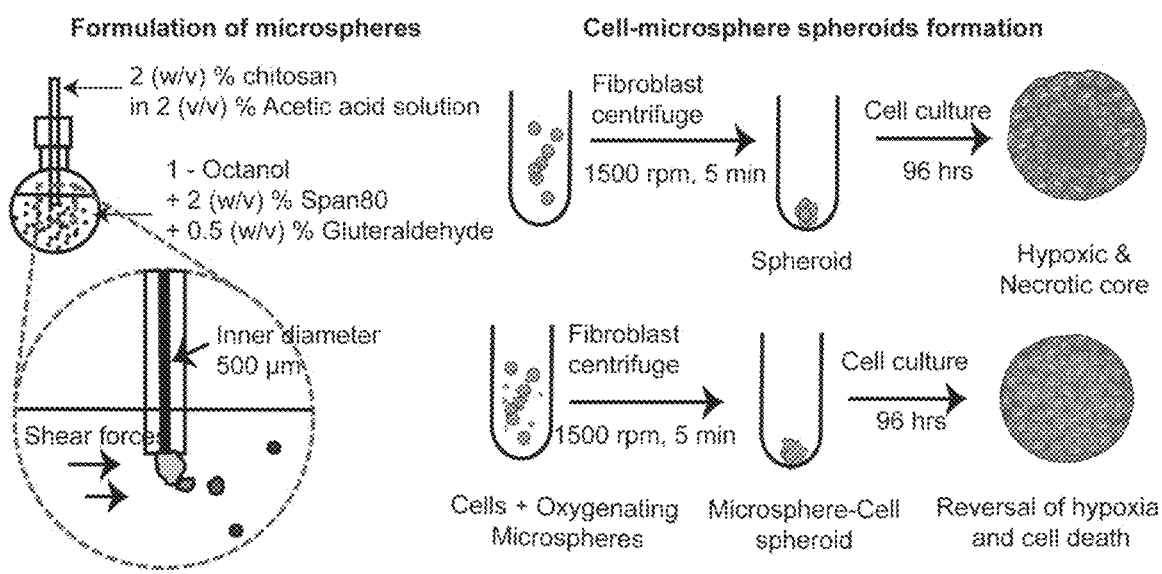
FIG. 2 is a representation of a mini-emulsion formulation of the fluorinated polymeric microparticles and then their combination with mammalian cells to form cell aggregates of the present invention.

In some embodiment, such as shown in FIG. 2, fluorinated polymeric microparticles are prepared by forming an emulsion of fluorinated polymers dissolved in an acidic buffer combined with an oily phase of a fatty alcohol with a surfactant. Specifically, the emulsion of fluorinated polymeric microparticles is formed by adding a solution of the fluorinated polymer and acidic buffer into a stirred solution of the fatty alcohol and surfactant. In some embodiments, the solution of the fluorinated polymer and acidic buffer are added to a stirred solution of the fatty alcohol and surfactant with the use of a syringe pump. In some embodiments, the speed at which the solution of the fatty alcohol and surfactant is stirred is between about 400 rpm and about 1600 rpm, in other embodiments between about 800 rpm and about 1500 rpm, and in yet other embodiments between about 1000 rpm and about 1400 rpm. In some embodiments, the speed at which the solution of the fatty alcohol and surfactant is stirred is at most 1600 rpm, in other embodiments at most 1500 rpm, and in yet other embodiments at most 1400 rpm. In some embodiments, the speed at which the solution of the fatty alcohol and surfactant is stirred is at least 400 rpm, in other embodiments at least 800 rpm, and in yet other embodiments at least 100 rpm. In embodiments, the solution of the fatty alcohol and surfactant was stirred at about 400 rpm, in other embodiments, at about 800 rpm, and, in yet other embodiments, at 1200 rpm. It was found that stirring of the solution of the fatty alcohol and surfactant at high stirring speeds lead to the formation of uniformly distributed smaller sized microparticles, whereas lower stirring speeds lead to the formation of larger non-uniformly sized microparticles.

In some embodiments, the solution of the fluorinated polymer and acidic buffer are added into the stirred solution of the fatty alcohol and surfactant at a rate of between about 1 µL/min and about 30 µL/min, in other embodiments, between about 2 µL/min and about 20 µL/min, and, in yet other embodiments, between about 3 µL/min and about 10 µL/min. In some embodiments, the solution of the fluorinated polymer and acidic buffer are added into the stirred solution of the fatty alcohol and surfactant at a rate of at least 1 µL/min, in other embodiments at least 2 µL/min, and in yet other embodiments at least 3 µL/min. In some embodiments, the solution of the fluorinated polymer and acidic buffer are added into the stirred solution of the fatty alcohol and surfactant at a rate of at most 30 µL/min, in other embodiments at most 20 µL/min, and in yet other embodiments at most 10 µL/min. In some embodiments, the solution of the fluorinated polymer and acidic buffer are added into the stirred solution of the fatty alcohol and surfactant at a rate of about 5 µL/min. Once formed, the fluorinated polymeric microparticles are then crosslinked with a crosslinking reagent in a stirred solution of a fatty alcohol and surfactant. This mentions "fluorinated polymer" being crosslink This step of crosslinking locks the microparticles into place so as to be able to easily transfer them out of the oily phase. Crosslinking covalently connects the long chains of the fluorinated polymer together with itself. In one embodiment of the present invention, the fluorinated polymeric microparticles are crosslinked for a period of about 2 hours. Once crosslinked, the microparticles are filtered and washed, and then freeze-dried.

In one or more embodiments of the present invention, the acidic buffer is selected from the groups consisting of acetic acid, hydrochloric acid, and combinations thereof. In one or more embodiments of the present invention, the fatty alcohol is selected from the group consisting of n-octanol, paraffin oil, or substituted with a solvent including hexane, ethyl acetate and combinations thereof. In one or more embodiments of the present invention, the surfactant is selected from the group consisting of any non-ionic surfactant such as those selected from the group consisting of sorbitan oleate, emulsifying waxes, polysorbate, ceteareth, Glycerin, Glyceryl Stearate, Lecithin, Polyglyceryl Oleate, Sorbitan Stearate, Glycol Oleate, PEG (polyethylene glycol), glycol, Shea Butter Glycerides, sodium tetraborate and combinations thereof. In one or more embodiments of the present invention, the crosslinking reagent is selected from the group consisting of glutaraldehyde, NH esters, imidoesters, carbodiimides, UV-initiated free radicals, ammonium persulphate, and combinations thereof. In one or more embodiments of the present invention, the fatty alcohol used during the crosslinking step is selected from the group consisting of n-octanol, paraffin oil or substituted with a solvent including hexane, ethyl acetate, hexadecane and combinations thereof. In one or more embodiments of the present invention, the surfactant used during the crosslinking step is selected from the group consisting of any non-ionic surfactant such as those selected from the group consisting of sorbitan oleate, emulsifying waxes, polysorbate, ceteareth, Glycerin, Glyceryl Stearate, Lecithin, Polyglyceryl Oleate, Sorbitan Stearate, Glycol Oleate, PEG (polyethylene glycol), glycol, Shea Butter Glycerides, sodium tetraborate and combinations thereof.

In one embodiment of the present invention, the fluorinated polymer is pentafluorooctanoyl-chitosan, the acidic buffer is acetic acid, the fatty alcohol is n-octanol, the surfactant is a sorbitan oleate (Span® 80), the crosslinking reagent is glutaraldehyde, the fatty alcohol used during the crosslinking step is n-octanol, and the surfactant used during the crosslinking step is a sorbitan oleate (Span® 80).

Once the fluorinated microparticles have been prepared, they can be combined with mammalian cells to create cell aggregates having increased oxygenation, such as shown in FIG. 2. The present invention defines the term "increased oxygenation" as being any cell aggregate loaded with fluorinated microparticles that has a partial oxygen pressure ($P_{O_2}$) 24 hours after being loaded with microparticles that is greater that the $P_{O_2}$ of the cell aggregate at the time of loading with the microparticles. Another way in which to define the term "increased oxygenation" is being any cell aggregate loaded with fluorinated microparticles that has a $P_{O_2}$ 24 hours after loading that is greater than any cell aggregate not loaded with fluorinated microparticles 24 hours later.

In one embodiment of the present invention, cell aggregates having increased oxygenation created in vitro using a combination of fluorinated polymeric microparticles and mammalian cells. In one embodiment, the cell aggregate having increased oxygenation are created by combining fluorinated polymeric microparticles in a centrifuge with mammalian cells. In one or more embodiments of the present invention, the centrifuge is spun at a speed from between about 200 rpm to about 2000 rpm, in other embodiments from about 300 rpm to about 1800 rpm, and in yet other embodiments from about 400 rpm to about 1600 rpm. In one or more embodiments, the centrifuge is spun at a speed of at most about 2000 rpm, in other embodiments at most about 1800 rpm, and in yet other embodiments at most about 1600 rpm. In one or more embodiments, the centrifuge is spun at a speed of at least about 200 rpm, in other embodiments at least about 300 rpm, and in yet other embodiments at least about 400 rpm. In one embodiment of the present invention, the centrifuge is spun at about 1200 rpm.

In some embodiments, the cell aggregate having increased oxygenation are created using a combination of fluorinated polymeric microparticles and human cells. In one or more embodiments of the present invention, the human cells are selected from the group consisting of dermal fibroblasts, stem cells, neural stem cells, liver cells (e.g., hepatocytes, stellate cells, sinusoid cells), neural stem cells, intestinal epithelia cells, stomach cells, colon cells, kidney cells, pancreas cells, lymphatic cells, vascular cells, bone cells, bone marrow cells, cardiac cells, brain cells, nerve cells, spinal cord cells, skin cells, fat cells, cancer cells, glandular cells, or reproductive cells.

In some embodiments, prior to being combined with the fluorinated polymeric microparticles, the mammalian cells are expanded to a ninth passage in a solution of a liquid growth media containing 10% of a cell growth additive and 100 µg/mL of an antibiotic so as to prevent contamination This step serves to create enough cells to be able to make the cell aggregate. Once this step is complete, the mammalian cells can be combined with the fluorinated polymeric microparticles. They are combined and seeded at various densities, such as 500,000, 1,000,000, and 2,000,000 cells/cm$^2$ and at fluorinated polymeric microparticle loading percentages of between 75% and 10% (v/v).

In one or more embodiments of the present invention, the liquid media for growth is selected from the group consisting of DMEM (Debelco's Minimum Essential Medium), MEME (Minimum Essential Medium Eagle), IMDM (Iscove's Modified Dulbecco's Medium), RPMI (Roswell Park Memorial Institute 1640), F12 (Ham's Mixture F-12), McCoy's 5A medium, mTeSR media, StemFlex Medium, Essential 8 Medium, Neurobasal Medium, MesenPRO RS Medium, and combinations thereof.

In one or more embodiments of the present invention, the cell growth additive is selected from the group consisting of FBS (Fetal Bovine Serum), NEAA (non-essential amino acids), L-glutamine, N2 supplement, B27 supplement, NeuroCult supplement, Holo-Transferrin, recombinant growth factors, methylcellulose, 2-Mercaptoethanol, Insulin, Transferrin, Lipid Supplements, Cholesterol Supplements, MEM Vitamin Solution, Pluronic F68, Serum Replacements, Sodium Pyruvate, Yeast Solution, Supplement S7, G5 Supplement, KnockOut Serum Replacement, and combinations thereof.

In one or more embodiments of the present invention, the antibiotic added to prevent contamination is selected from the group consisting of actinomycin D, kanamycin, ampicillin, neomycin, carbenicillin, cefotaxime, polymyxin B, fosmidomycin, penicillin, streptomycin, gentamicin, amphotericin B (fungizone), and combinations thereof. In one embodiment of the present invention, DMEM is the liquid media for growth, FBS is the cell growth additive, and a combination of penicillin and streptomycin are the antibiotics used to prevent contamination.

The mini-emulsion method discussed above provides a fast and scalable process for formulating microparticles. The results of the present invention demonstrate that fluorinated polymeric microparticles formulated at a high speed (of about 1200 rpm in some embodiments), formed smaller particles with a narrow distribution. In terms of incorporation into cell aggregates, smaller sized microparticles maximize the benefit of oxygen transport to ensure adequate cell cohesion in sustaining cell aggregate formation and subsequent cell survival. Further, targeting particles with sizes on the order of a cell provides a benefit of cellular interaction while eliminating or reducing the chances of internalization of particles by the immune system in organoids if created for in vivo applications. Therefore, microparticle sizes of ~10-50 µm should provide cells a biomaterial surface to interact and enhance local oxygen transport.

Figure 3:
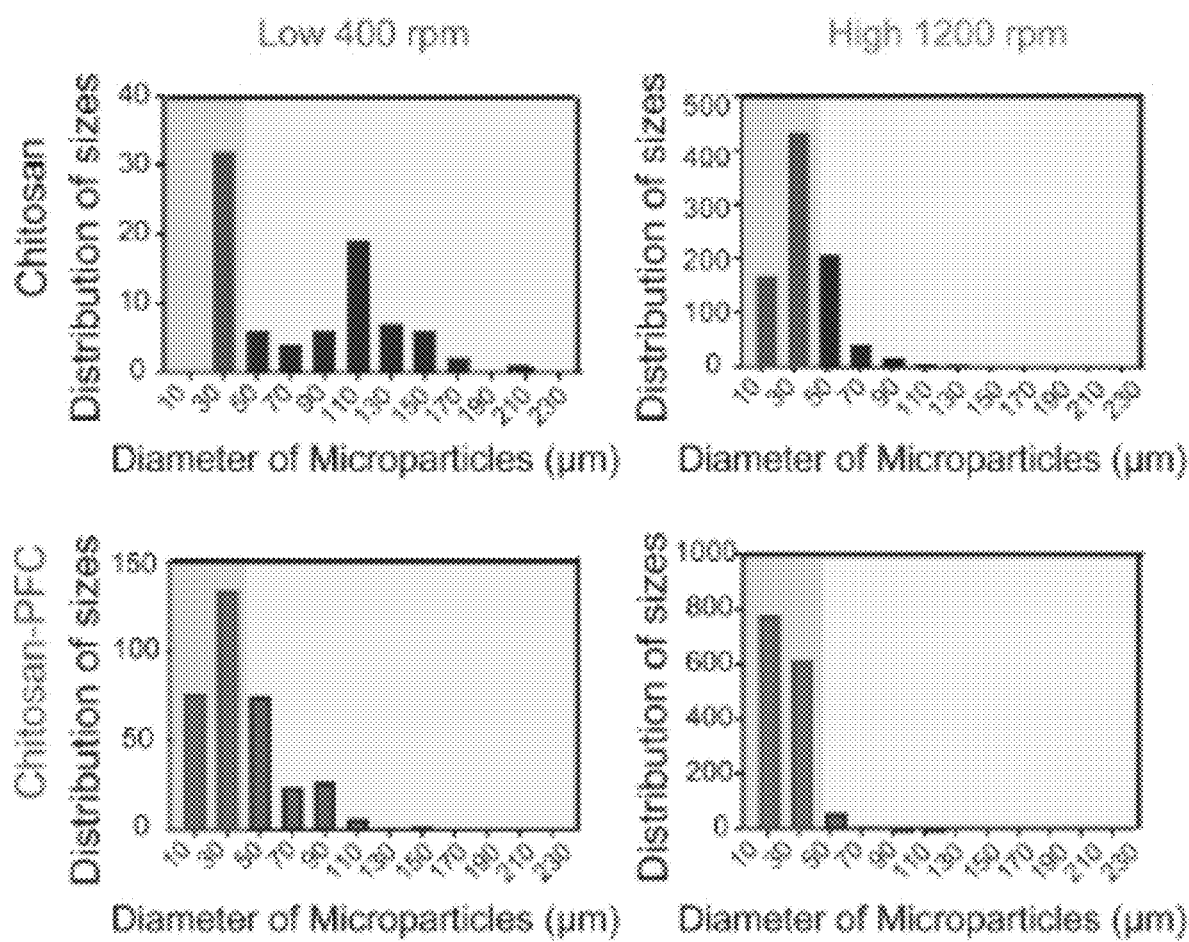
FIG. 3 is multiple graphs showing the distribution of sizes of chitosan and chitosan-PFC particles formulated at low (400 rpm) speed and high (1200 rpm) speed.

The findings of the present invention show that cell aggregates formed using 1 and 2 million cells per cell aggregate successfully sustained cell proliferation and cell aggregate growth. Centrifugation of cells in u-bottom well plates leads to the formation of dense cell aggregates. In the past, others have formed cell aggregates with cell densities of the order of ~0.1 million cells, likely in an attempt to reduce necrotic cores. High density cell aggregates are known to have a high oxygen diffusion barrier and hence tend to form a large hypoxic core. In the present invention, direct oxygen measurements of oxygen gradients in cell aggregate cultures were performed using $O_2$ sensors, and oxygen zonation was defined. Thus, as shown in FIG. 3, high density cell aggregates, like those containing on the order of 1 to 2 million cells lead to larger hypoxic and necrotic regions, unless addressed by combining with fluorinated polymeric microparticles.

Figure 4:
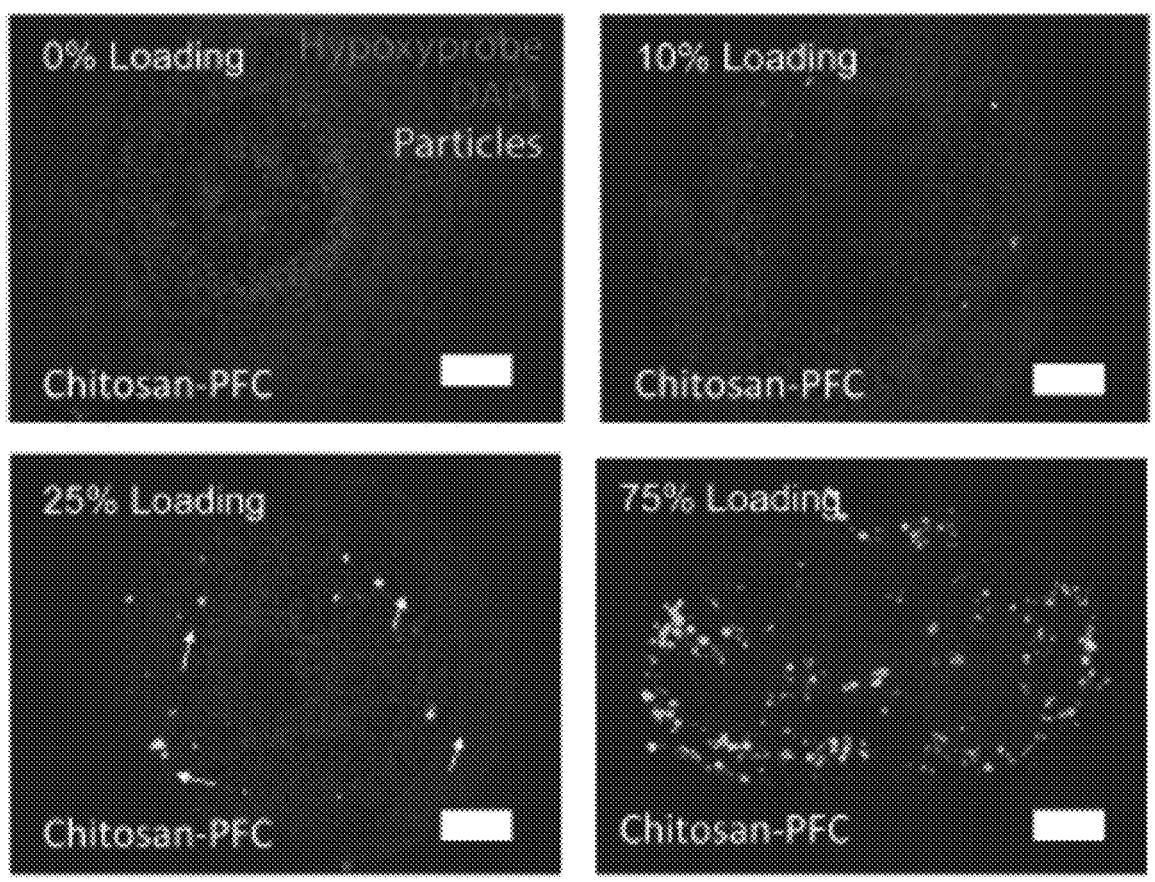
FIG. 4 shows images of cell aggregate sections of various loading percentages of the fluorinated polymeric microparticles.

The addition of fluorinated polymeric microparticles at different loading percentages imparts the ability to adjust hypoxic/necrotic responses. The findings of the present invention exhibit a trend that hypoxia in cell aggregates is reduced with increasing loading % of microparticles. FIG. 4 shows representative images of hypoxyprobe IHC (in red) which shows hypoxia in a cell aggregate section after 4 days in culture and wherein the presence of fluorinated polymeric microparticles are shown in yellow. As is shown in FIG. 4, a cell aggregate that does not include any fluorinated polymeric microparticles undergoes a large hypoxic/necrotic response, as shown by the red dye of the hypoxyprobe IHC. Also as shown in FIG. 4, the more fluorinated polymeric microparticles loaded into a cell aggregate leads to a smaller hypoxic/necrotic response, as shown by the smaller amount of red dye visible in these cell aggregates.

Figure 5A:
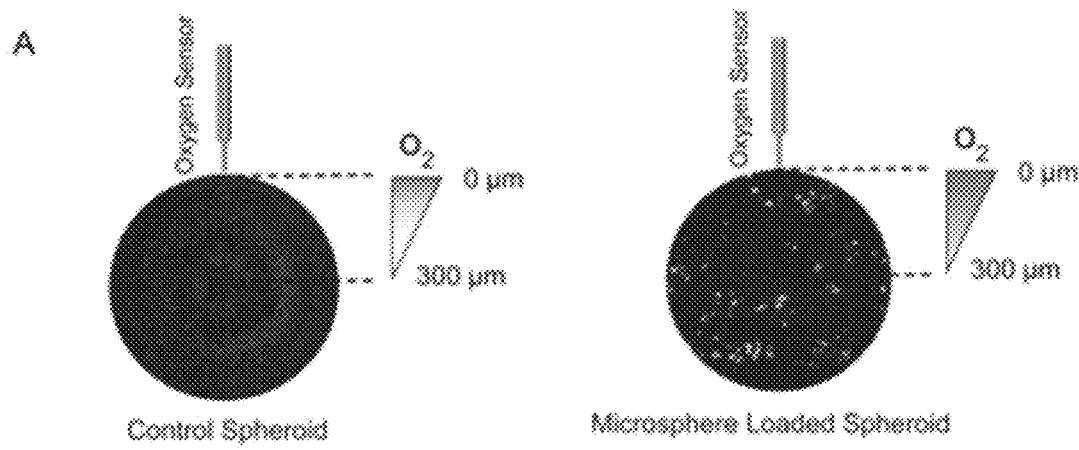
FIG. 5A shows how oxygen concentration was measured at various depths inside spheroids.
Figure 5B:
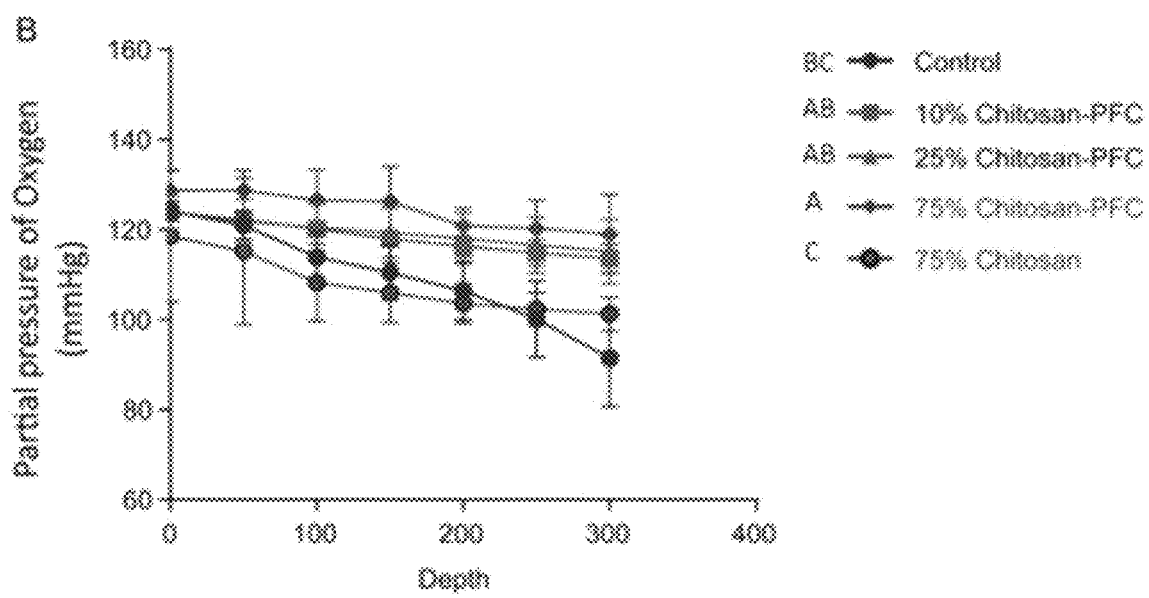
FIG. 5B shows the results of oxygen concentration measurement experiments as conducted with a control spheroid not loaded with fluorinated polymeric microparticles, with a spheroid loaded with 10% v/v fluorinated polymeric microparticles, with a spheroid loaded with 25% v/v fluorinated polymeric microparticles, with a spheroid loaded with 75% v/v fluorinated polymeric microparticles, and with a spheroid loaded with 75% v/v non-fluorinated polymeric microparticles.

Particles can be added about at 10% to about 75% volume percent initially to the cell aggregates. The findings of the present invention demonstrate and confirmed generally accepted findings that oxygen limitations are only significant above 100 µm diameter in cell aggregates. Further, the present invention reveals that it is possible to limit the cell aggregate hypoxic/necrotic region by limiting the size of the cell aggregate to smaller cell aggregates (<150 µm diameter). The present invention directly addresses the oxygen transport problem in micro-tissues and demonstrates the ability to create larger cell aggregates with smaller hypoxic and necrotic regions, such as shown in FIGS. 5A and 5B, thus overcoming previous size limitations. With 75% loading of the fluorinated polymeric microparticles in a cell aggregate, the hypoxia is almost negligible.

EXPERIMENTAL

The following examples are offered to more fully illustrate the invention, but are not to be construed as limiting the scope thereof. Further, while some of examples may include conclusions about the way the invention may function, the inventors do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Preparation of Pentafluorooctanoyl-Chitosan Microparticles

Pentafluorooctanoyl-chitosan was prepared and used to formulate microparticles utilizing a modified mini-emulsion method. Microparticles were prepared by forming an emulsion of 2% (w/v) fluorinated chitosan dissolved in 2% (v/v) acetic acid into a stirred solution of an oily continuous phase of n-octanol (Sigma Aldrich, St Louis, Mo.) with 2% (w/v) and span80 (Sigma Aldrich). Fluorinated chitosan was pumped at a rate of 5 µl/min into a solution of a fatty alcohol and surfactant that was being stirred at speeds of between about 400 rpm and about 1200 rpm using a syringe pump. Microparticles were crosslinked for 2 h using 0.5% (w/v) glutaraldehyde (Sigma Aldrich) in n-octanol with 2% (w/v) span80. Microparticles were filtered using 220 nm filter and washed with 70% ethanol 2 times followed by DI water 5 times. The microparticles were then freeze-dried and stored at 4° C.

Microparticle Size and Size Distribution Analysis

Formulated microparticles were dried in a desiccator for 24 h before the scanning electron microscopy (SEM). The sample was prepared from microparticles in powder form on carbon tape. Hitachi TM3030Plus-SEM was used for imaging microparticle surface morphology. Particles were imaged at 5 keV energy and 300× magnification in backscattered electrons mode, and particle analyzer plugin in Image J (National Institute of Health, Bethesda, Md.) software was used for particle size and distribution analyses. The median and interquartile range was calculated from distributions to study median and spread of the distribution and compare experimental treatments.

Oxygen Saturation Analysis

Formulated microparticles were re-suspended at a density of 50 mg/mL in fibroblast growth media (Dulbecco's modified eagle medium (DMEM)+10% fetal bovine serum (FBS)). Then, the particles were passed through 70 µm cell strainer to filter out the larger particles. The filtrate was taken as it has particles smaller than 70 µm. These particles were counted using hemocytometer and used for the oxygen saturation experiment at 20,000 particles/mL concentration. Particles prepared from chitosan-PFC and chitosan were compared against a media-only control. Well plates with 1 mL suspension of each were placed in a 37° C. incubator. Oxygen partial pressure was measured by FireSting O2 II (Pyro Science, Aachen, Germany) device with optical sensor spots immersed in media suspension. Data was logged using FireSting O2 software (OxyView PST6-V5.41). The experiment was considered complete when suspension had reached an oxygenated equilibrium such that the change was less than 0.1% partial pressure of oxygen ($P_{O2}$) per minute Cell and Chitosan-PFC Microparticles Aggregate Spheroids First, the spheroids with cells only were formed in vitro using human dermal fibroblasts harvested from neonatal foreskins. The fibroblasts were expanded to a ninth passage in DMEM containing 10% FBS and 100 µg/mL penicillin-streptomycin (all Life Technologies; Carlsbad, Calif., USA). They were then seeded at a density of 500,000; 1,000,000 and 2,000,000 cells/cm2 in non-adherent U bottom Nunclon 96-well Sphera plates (Thermo-Fischer Scientific, Waltham, Mass.). Aggregation was initiated by spinning 96 U bottom well plates in a centrifuge at 250 G for five minutes at room temperature. The cell spheroids were allowed to grow for four days in an incubator at 37° C. and 5% $CO_2$. On the fourth day, spheroids were imaged with an optical microscope and sizes were analyzed using Image J (National Institute of Health, Bethesda, Md.).

Next, aggregates were prepared by seeding cells with fluorinated chitosan microparticles at 75, 50, 25, 10 and 0% (v/v). Aggregation was initiated by spinning 96 U bottom well plates in a centrifuge at 250 G for five minutes at room temperature. The cell spheroids grew for four days in an incubator at 37° C. and 5% $CO_2$. On the fourth day, spheroids were incubated with 100 µM Pimonidazole HCl (Hypoxyprobe Inc., Burlington, Mass.) in media. Spheroids were then imaged with an optical microscope and were fixed using 3.7% paraformaldehyde. After fixing, spheroids were cryosectioned in OCT and IHC was performed. The region of the necrotic core was measured by measuring the diameter of the core using image analysis Finally, high loading percentage aggregates were prepared by seeding cells with fluorinated chitosan microparticles, chitosan microparticles and sham at 75% microparticles per aggregate. Spheroids were allowed to grow as discussed previously. Cell microparticle aggregates were incubated with 100 µM Hypoxyprobe™ (Hypoxyprobe, Burlington, Mass., USA) at room temperature for one to two hours. Then, they were kept in a solution of sucrose until it sunk and then an equal amount of OCT was added (blue is preferred to visualize spheroids) and they were then kept at 4° C. overnight. Next day, the solution was centrifuged and embedded in OCT and stored frozen at −80° C. until ready for sectioning. Cell microparticle aggregates were cryosectioned to get a section at the middle of the aggregate. IHC was performed followed by imaging and image analysis. The other half of spheroids (n=3) were digested in radio-immunoprecipitation assay buffer (RIPA) to isolate ds-DNA. Total DNA assay was performed using Quant-iT™ Pico Green double stranded DNA (dsDNA) assay (Life Technologies, Carlsbad, Calif.) using manufacturer's protocol. Fluorescence was measured using the Infinite M200 spectrofluorometer (Tecan, Maennedrof, Switzerland) (at an excitation wavelength of 480 nm and an emission wavelength of 520 nm) to reveal the total dsDNA mass in each well. Total dsDNA is directly proportional to live cells, therefore, this assay indicates how many cells are included in each spheroid and thus the effectiveness of the present invention.

Immunohistochemistry, Microscopy, and Image Analysis

A standard IHC protocol with 1/200 dilution for primary affinity purified rabbit anti-pimonidazole antibody (PAb2627AP) to detect hypoxyprobe substrate/antigen and 1/500 for secondary Goat Anti-Rabbit IgG (H+L) Highly Cross-Adsorbed Antibody, Alexa Fluor 594 was used. Sections were counterstained with Hoechst 33342 for nuclei. Post-staining, all tissues were washed with 1×PBS three times and imaged using 4',6-diamidino-2-phenylindole (DAPI), green fluorescent protein (GFP) and cyanine 5 (CY5) fluorescence filters with an Olympus epifluorescent microscope (Olympus IX-81, Tokyo, Japan). Fluorescent microscopy images were obtained and analyzed to quantify the hypoxyprobe intensity and necrotic region. Image J software was used for image analysis to calculate hypoxyprobe intensity and size of the necrotic region.

All the statistical analyses were performed using JMP 13 (SAS Institute, Cary N.C., USA). ANOVA with Tukey's post hoc analysis was performed to detect significant differences between groups. An α level of 0.05 was used to determine significance between groups, a p-value<0.0001 is considered highly significant. Data were reported as the mean±standard deviation (SD).

Results

The size and size distribution analysis of the chitosan and chitosan-PFC microparticles partially elucidate the effect of stirring speed on microparticle sizes. At low rpm, the particle size of chitosan (67.9±47.7 µm) was similar to chitosan-PFC (40.7±25.1 µm). This trend was also observed at high rpm with chitosan (35.4±19.4 µm) and chitosan-PFC (22.3±8.9 µm) sizes. The results, such as those shown in FIG. 3, show that stirring speed affected the microparticle sizes, and particles prepared at a low stirring speed of 400 rpm were larger compared to particles prepared at a high stirring speed of 1200 rpm.

Size distribution analysis provided vital insight into dispersity of the microparticles. The spread of the distribution calculated as an interquartile range of chitosan particles prepared at low stirring speeds was 83.9 µm, which was the highest amongst all groups, followed by chitosan-PFC prepared at low stirring speeds was 31.2 µm. The size distribution of chitosan and chitosan-PFC prepared at high stirring speeds had a spread of 20.3 µm and 8.8 µm respectively. Chitosan-PFC microparticles prepared at low stirring speeds of about 400 rpm had a median of 34.5 µm and chitosan-PFC microparticles prepared at high stirring speeds of about 1200 rpm had a median of 19.5 µm, whereas, chitosan microparticles prepared at low stirring speeds of about 400 rpm had a median of 66.9 µm and chitosan microparticles prepared at high stirring speeds of about 1200 rpm has a median of 34.1 µm.

Oxygen adsorbing/transport properties in PBS were studied using 5% $CO_2$ incubator and measuring oxygen saturation at 0 and 24 h. It was observed that the suspension of chitosan-PFC microparticles sequestered a $P_{O2}$ of 162.8±1.1 mmHg after 24 hours as compared to starting partial pressure of 156.7±0.9 mmHg at 0 hours and the PBS control at $P_{O2}$ of 158.20±0.1 mmHg at 24 hours. The oxygen content of PBS only control was similar after 24 hours. The starting oxygen partial pressure of both PBS control and chitosan-PFC was similar.

To optimize spheroid size for microparticle experiments, spheroids of different cell densities were formed, and sizes were measured using optical microscopy. This analysis revealed that the cell density linearly affects spheroid sizes. Spheroids with 2 million cells were larger in size as compared to both spheroids with 1 million and 500,000 cells. As the expected size of 1 million cell spheroid was larger as compared to 500,000 cell spheroids. Thus, spheroids with 2 million cells were selected for further experiments.

As a next step, the response of increasing microparticle loading on hypoxia in spheroids was studied. 1 million cells spheroids with 0, 10, 25, 50, 75 v/v % loading of chitosan-PFC microparticles were prepared and sectioned. The spheroids were then stained for hypoxyprobe. The extent of hypoxia was determined by measuring hypoxyprobe intensity using image analysis. Hypoxyprobe intensity was significantly reduced upon incorporation of 10, 25 and 75 v/v/% microparticles. Microparticle loading of 10% resulted in reduced hypoxyprobe intensity as compared to the no loading control and one-factor ANOVA. Interestingly, the hypoxyprobe intensity was found to be the same for 10 and 25% loading. In addition to quantifying hypoxia, the region of the necrotic core was measured by measuring the diameter of the core using image analysis. It was found that the necrotic region size depended on the loading % of chitosan-PFC microparticles. The necrotic region was significantly reduced upon 50% loading of microparticles in the spheroids as compared to all other groups. Surprisingly, it was found that the loading percentage of 10 and 25 were not distinct in the reduction of necrotic region sizes but both were significantly reduced as compared to the no loading group.

To test the effect of 75 v/v % loading of microparticles, spheroids with chitosan and chitosan-PFC were each prepared with a loading percentage of 75% and they were compared against spheroids prepared without any microparticles. Hypoxyprobe intensity was measured, and total ds-DNA was analyzed. Hypoxyprobe intensity was seen to be significantly lower in the 75% loaded chitosan-PFC microparticles as compared to both the chitosan loaded group and no microparticles group. Surprisingly, ds-DNA results demonstrated that the chitosan-PFC group had higher amounts of ds-DNA than chitosan microparticle loaded spheroids. Both chitosan-PFC and chitosan loaded spheroids had a comparable amount of ds-DNA as compared to non-loaded spheroids (p=0.39 and p=0.23, respectively) but chitosan-PFC trends slightly higher. Double stranded DNA amount (ds-DNA) is a direct measure of cell number, thus the more ds-DNA the more cells are present in the spheroid. Thus, the chitosan-PFC microparticle treatment allows for more cells to exist, likely via a combination of reduced death and increased proliferation.

As shown in FIGS. 5A and 5B, oxygen measurements at various depths in the spheroids revealed that increased loading percentages of chitosan-PFC microparticles corresponded with reduced steepness of oxygen concentration gradients from the periphery to the center of the spheroid. Illustratively, the chitosan microparticle loaded spheroids exhibited lower oxygen concentrations at the periphery and near the center. Conversely, chitosan-PFC microparticle loaded spheroids showed improvement in oxygen concentrations near the center with increasing loading of 10, 25, and 75% of the microparticles. Expectedly, the control spheroids without any microparticles showed a sharp decrease in oxygen periphery near the center. The oxygen concentration near the center of the spheroids loaded with fluorinated polymeric microparticles was found to be significantly higher in spheroids loaded with 10% chitosan-PFC (p=0.027), 25% chitosan-PFC (p=0.019), and 75% chitosan-PFC (p=0.015) as compared to non-loaded spheroids. These results support the premise that diffusion barriers to oxygen in spheroids can be reduced by enhancing oxygen transport properties of spheroids, and PFCs are well-suited suited for this purpose based on their high affinity for oxygen as well as carbon dioxide.

In light of the foregoing, it should be appreciated that the present invention significantly advances the art by providing a method for obtaining multicellular aggregates/spheroids having increased oxygenation that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A method for obtaining cell aggregates having increased oxygenation, the method comprising:
preparing fluorinated polymeric microparticles with a size of from about 10 µm to about 50 µm; and
combining the fluorinated polymeric microparticles with mammalian cells to create the cell aggregates having increased oxygenation.

2. The method of claim 1, wherein the step of preparing the fluorinated polymeric microparticles utilizes a method selected from the group consisting of a mini-emulsion method, electro-spraying, microfluidics, and flow focusing.

3. The method of claim 2, wherein the method is a mini-emulsion method and wherein the mini-emulsion method includes the steps of pumping a solution of a fluorinated polymer and an acidic buffer into a stirred solution of a fatty alcohol and a surfactant using a syringe pump and then crosslinking with a crosslinking reagent.

4. The method of claim 3, wherein the fluorinated polymer includes polymers having polysaccharide backbone chains and wherein the polysaccharide backbone chains have a pendant fluorine containing group attached thereto.

5. The method of claim 4, wherein the polysaccharide backbone chains include a polysaccharide unit defined by the formula:

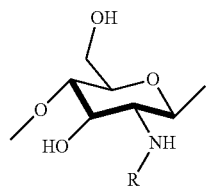

where R is a fluorine containing group.

6. The method of claim 4, wherein the polysaccharide backbone chains include one or more saccharide units that include an alkene group selected from the group consisting of:

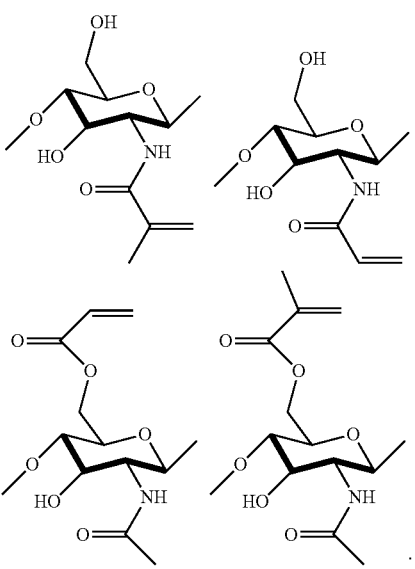

7. The method of claim 4, wherein the fluorinated polymer is defined by the formula:

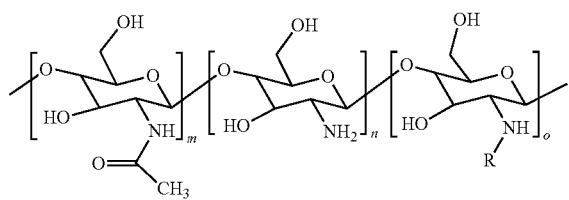

where R is a fluorine containing group, m is about 0% to about 20% of the total saccharide units, n is about 50% to about 95% of the total saccharide units, and o is about 1% to about 40% of the total saccharide units.

8. The method of claim 3, wherein the solution of the fluorinated polymer and the acidic buffer is pumped into the stirred solution of the fatty alcohol and surfactant at a rate of between about 1 µL/min to about 30 µL/min.

9. The method of claim 3, wherein the solution of the fluorinated polymer and the acidic buffer is pumped into the solution of the fatty alcohol and surfactant that is being stirred at a rate of between about 400 rpm and about 1200 rpm.

10. The method of claim 1, wherein the mammalian cells are selected from the group consisting of dermal fibroblasts, stem cells, neural stem cells, liver cells including hepatocytes, stellate cells, and sinusoid cells intestinal epithelia cells, stomach cells, colon cells, kidney cells, pancreas cells, lymphatic cells, vascular cells, bone cells, bone marrow cells, cardiac cells, brain cells, nerve cells, spinal cord cells, skin cells, fat cells, cancer cells, glandular cells, or reproductive cells.

11. The method of claim 1, wherein the cell aggregates having increased oxygenation have a partial oxygen pressure 24 hours after being combined with the fluorinated polymeric microparticles that is greater that the partial oxygen pressure of the mammalian cells at the time of combination with the fluorinated polymeric microparticles.

12. The method of claim 1, wherein the fluorinated polymeric microparticles are combined with the mammalian cells in a centrifuge at a speed of from about 200 rpm to about 2,000 rpm.

13. The method of claim 1, wherein the obtained cell aggregate contain between about 10% and about 75% volume percent of the fluorinated polymer microparticles.

* * * * *